United States Patent [19]

McRae

[11] Patent Number: Plant 6,476

[45] Date of Patent: Dec. 20, 1988

[54] LILY NAMED PINK PIXIE

[75] Inventor: Edward A. McRae, Boring, Oreg.

[73] Assignee: Melridge, Inc., Gresham, Oreg.

[21] Appl. No.: 23,779

[22] Filed: Mar. 9, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant of short stature, about eighteen inches, bearing large clusters of flowers particularly characterized by their deep pink, cream-centered coloration borne upright in a compact raceme arrangement and comprising from five to nine buds. The short stature of this plant, its moderately long and full leaves, and its medium sized, upright flowers make it especially suitable as a pot plant variety. The color pattern and silhouette of this new plant are completely new in the upright Asiatic divisions of lilies suited to forcing for mass commercial cultivation. The plant is highly resistant to disease and shows high tolerance of virus, which makes it an excellent garden plant; and the bulbs may be precooled and forced throughout the year for pot plant production.

1 Drawing Sheet

BACKGROUND OF THE NEW PLANT

This new lily plant variety originated as a seedling selected from a group of seedlings of a plant resulting from my crossing the clonal cultivar 'Peachblush' (unpatented) as the seed parent with a shorter pink seedling selected from the cross of 'Prince Charming' and 'Harmony' (both unpatented). This crossing was done at Sandy, Oreg., with the objective of producing lilies in the shades of pink and peach, well suited for forcing for pot plant production out of season. The selected seedling was one of the said group having a very unusual deep pink, cream-throated coloration with copious spotting in the center of the flower and because this color pattern was unique in this type of lily, this particular seedling was chosen for propagation. Asexual propagation of this selected seedling was done by me and under my direction at Sandy, Oregon, by bulb scale propagation with such satisfactory results that production was continued through several successive generations by bulb scale propagation and by bulblets and it was thereby demonstrated that the novel characteristics of this seedling would hold true from generation to generation and appeared to be firmly fixed.

Work with this new plant has demonstrated that the variety remains short and is not overly susceptible to bud abortion when forced into flower out of season as a pot plant. In addition, the clone possesses to a high degree the desirable characteristics of hybrid vigor, great hardiness, and disease resistance.

This new plant is well suited to forcing out of season when the bulbs are dug at the appropriate time and properly precooled. For example, October-dug bulbs, properly precooled and potted in January, will flower under glass in western Oregon in an average of sixty-five to seventy-five days, with no supplementary lighting and at moderate greenhouse temperatures.

DESCRIPTION OF THE DRAWING

My new lily plant variety is illustrated by the accompanying photographic drawing which, in full color, shows the open bloom and illustrates the flower form, the tepal arrangement, and the copious spotting of the cream-colored base portion of the tepals which collectively forms a ring encircling the center of the flower.

DESCRIPTION OF THE NEW VARIETY

The following is a detailed description of my new Asiatic hybrid lily variety, with nomenclature according to The International Lily Register (The Royal Horticultural Society of London, England, 2nd Edition, 1969) and with color designations according to The R.H.S. Colour Chart of The Royal Horticultural Society published by that society in 1966.

THE PLANT

Origin: Seedling.

Parentage:

*Seed parent.*—Lilium 'Peachblush' (unpatented).

*Pollen parent.*—A short, pink-flowered hybrid Lilium seedling selected from the cross of 'Prince Charming' and 'Harmony' (both unpatented).

Classification:

*Horticultural.*—Division I-A, upright Asiatic hybrid lily according to the Horticultural Classification of Lilies (The Royal Horticultural Society of London).

Form: A single stem, erect and stately.

Height: About 45 to 50 cm. as produced by glasshouse forcing of bulbs of about 12 to 18 cm. in circumference, provided that their light levels are adequate; low light levels may cause "stretching".

Growth: Vigorous and upright.

Foliage:

*Quantity.*—Abundant

*Size of leaf.*—About 12 to 16 cm. long and about 0.5 to 1 cm. wide.

*Shape of leaf.*—Lanceolate and acuminate.

*Texture.*—Leathery

*Aspect.*—Glossy and lightly pubescent.

*Color.*—Dark green, lighter on the lower side.

The Bulb:

*Size.*—Varying, ranging to about 25 cm. in circumference in commercial use.

*Color.*—White

THE BUD

Form: Long ovoid with obtuse tip and rounded base.

Size: About 8 to 9 cm. long and about 5 cm. in circumference just prior to opening.

Opening rate: The bud opens slowly taking about one hour in response to morning light.

Color: Soft pink with a flush of green along the midribs and at the tip, prior to opening and as the tepals unfurl. Lightly pubescent.

Peduncle:

*Length.*—About 4 to 6 cm., in average. The peduncle may elongate if light levels are too low or if the bulbs have been improperly stored prior to forcing.

*Color.*—Dark green.

THE FLOWER

Blooming habit: Once annually and profusely in midseason.

Size: About 13 to 15 cm. in diameter.

Borne: In a single compact raceme producing 5 to 9 buds from a bulb of about 12 to 16 cm. in circumference.

Shape: Cup-shaped when first opened and flattening as the tepals recurve by the second day.

Tepalage: Typical of genus Lilium with six imbricated and hexagonally arranged tepals.

*Size.*—The outer tepals averaged about 2.5 cm. in width and the inner tepals average about 3 cm. in width.

*Color.*—Mainly a deep pink, 58B, overlaying a cream to straw colored throat of yellow-orange, 18A/B, which extends about 4 to 4.5 cm. from the base of the tepal. There is a softer pink flush about 1 cm. long at the extreme base of each tepal. The nectaries are cream to pink in color and pubescent.

*Spotting.*—The tepals are copiously spotted with small to medium sized magenta spots throughout the base third of each tepal, thereby forming a ring about 3 cm. wide, above the nectaries and encircling the center of the flower.

*Aspect.*—Shiny

*Color changes.*—The flowers may lighten slightly to 58D at the tips as the flowers age. Strong heat and light can reduce the pink pigmentation but there is little change in flower colors if light and temperature levels are suitable for cut flower and pot plant maintenance.

*Persistence.*—The tepals stay on the stems about three weeks.

Pedicel:

*Length.*—About 4 to 8 cm., in average.

*Color.*—Dark green, lightly pubescent.

*Character.*—Sturdy and ascending up to about 60 degrees from the horizontal.

Disease resistance: The plant and its flower are resistant to disease. In particular, they are resistant to Fusarium bulb rot and Botrytis blight.

Lasting quality: The flower is long lasting, both on the plant and as a cut flower.

REPRODUCTIVE ORGANS

Stamens:

*Number.*—Six, with arrangement typical of genus Lilium.

*Anthers (dehisced) and pollen.*—Color: Greyed orange, 171A.

*Filaments.*—Length: About 5 cm. Color: 18C to 36A.

Pistil:

*Number.*—One.

*Style.*—About 5 cm. long.

*Stigma.*—Size: Medium to large. Color: Deep plum.

Character of ovary: The ovary is characteristic of genus Lilium.

THE FRUIT

Fertility: The fruit is fertile.

Shape: Ovoid

Color at maturity: Soft brown, sometimes overlaid with soft plum.

This new lily plant most closely resembles the variety 'Peachblush' (unpatented) but it has a pinker and less peach-toned coloration with a lighter-toned cream to straw colored center with much more conspicuous spotting. The new plant also has a more compact inflorescence with shorter pedicels, a somewhat shorter height, and more abundant and narrower leaves.

I claim:

1. The new and distinctive variety of Asiatic hybrid lily and parts thereof, substantially as herein shown and described, particularly characterized by the deep pink principal coloration of the tepals with a cream-colored throat portion in the center of the flower, and by its short, abundantly leaved silhouette.

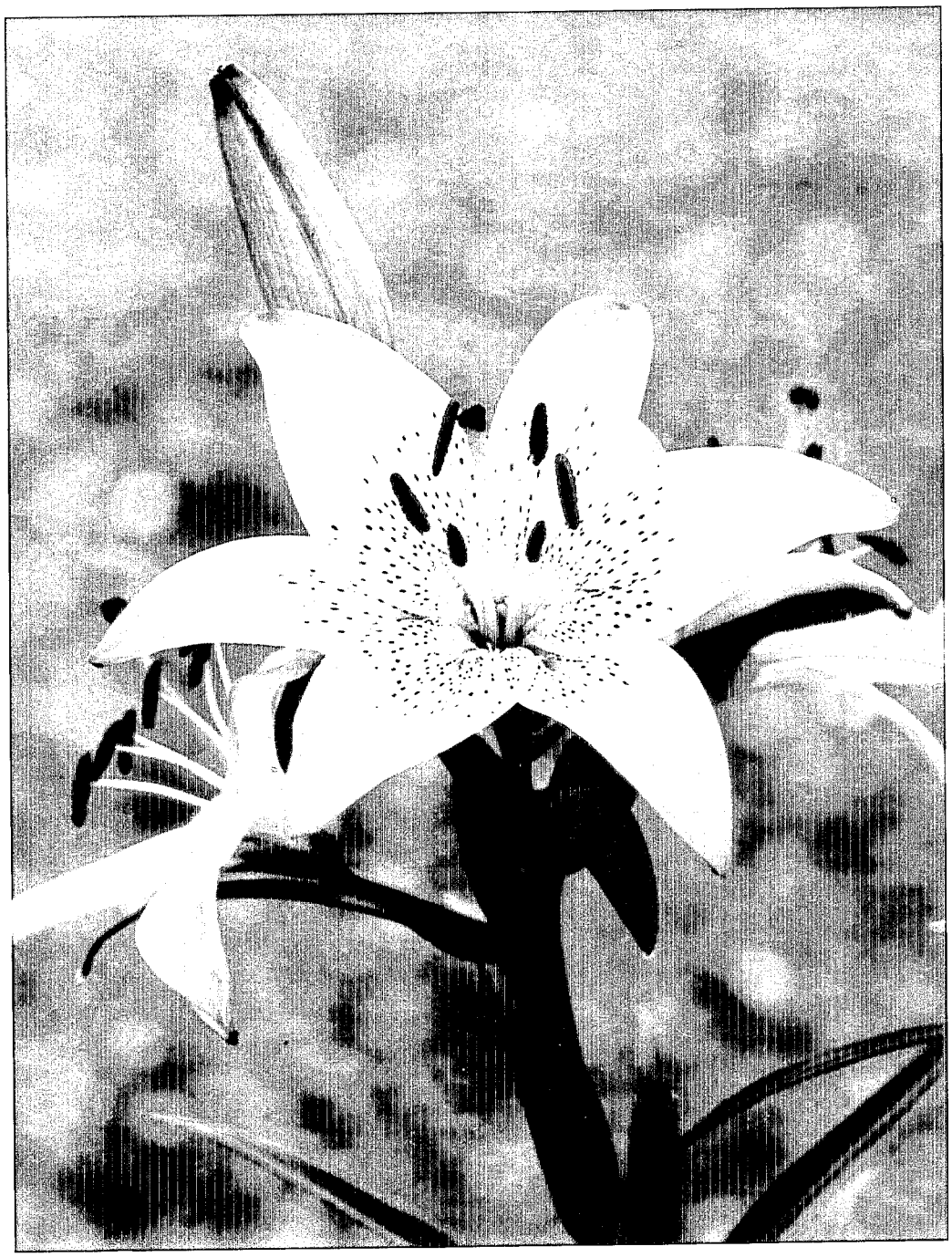

* * * * *